United States Patent [19]

Weder et al.

[11] Patent Number: 5,658,898

[45] Date of Patent: Aug. 19, 1997

[54] INTRAVENOUS SOLUTIONS FOR A DERIVATIVE OF STAUROSPORINE

[75] Inventors: Hans Georg Weder, Rüschlikon, Switzerland; Ute Isele, Ihringen, Germany

[73] Assignee: CIBA GEIGY Corporation, Tarrytown, N.Y.

[21] Appl. No.: 553,126

[22] Filed: Nov. 7, 1995

[30] Foreign Application Priority Data

Nov. 9, 1994 [CH] Switzerland .............................. 3375/94
Mar. 2, 1995 [CH] Switzerland .............................. 595/95

[51] Int. Cl.$^6$ .......................... A61K 31/55; A61K 9/127
[52] U.S. Cl. .......................... 514/211; 514/937; 424/450
[58] Field of Search .................................. 514/211, 937; 424/450

[56] References Cited

U.S. PATENT DOCUMENTS 5,093,330  3/1992  Caravatti et al. ..................... 514/211
5,152,923  10/1992  Weder et al. ......................... 252/312

FOREIGN PATENT DOCUMENTS 9522331  8/1995  WIPO.

*Primary Examiner*—Theodore J. Criares
*Attorney, Agent, or Firm*—Marla J. Mathias; Gregory D. Ferraro

[57] ABSTRACT

The invention relates to a novel advantageous dosage form for sparingly soluble staurosporin derivatives, especially N-benzoyl-staurosporin. The dosage form is administrable intravenously in the form of a nanoemulsion and comprises as solubilisers a combination of phospholipids, triglycerides and partial fatty acid esters of polyoxyethylene sorbitan.

7 Claims, No Drawings

INTRAVENOUS SOLUTIONS FOR A DERIVATIVE OF STAUROSPORINE

The present invention relates to a pharmaceutical composition for the intravenous administration of a sparingly soluble staurosporin derivative, to a process for the preparation of said composition and to the use thereof in therapy.

The starting material of numerous derivatives, staurosporin, was isolated in 1977 from cultures of Streptomyces staurosporeus AWAYA, TAKAHASHI, OMURA SP. NOV. AM 2282, see S.Omura et al., J. Ant. 30, 275–281 (1977). For the skeletal structure, first the relative configuration and then the absolute configuration was determined, see N.Fumato et al., Tetrahedron Letters 35:8, 1251–1254 (1994). The following structural formula is assigned to the especially preferred N-benzoyl-staurosporin derivative, which is described in U.S. Pat. No. 5,093,330:

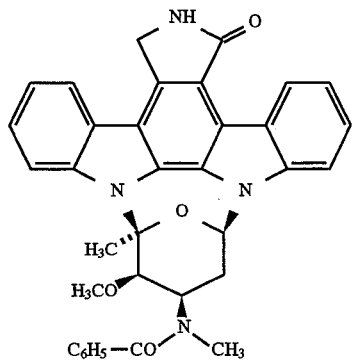

Staurosporin and its derivatives, such as N-benzoyl-staurosporin, effect a strong inhibition of protein kinase C, but also likewise inhibit other protein kinases. They are therapeutically applicable for various indications, especially as tumour inhibitors, as anti-inflammatory agents, as antibiotics, and in the treatment of arteriosclerosis and various disorders of the cardiovascular system and central nervous system. A characteristic property of staurosporin and most derivatives thereof is their low water-solubility, which has hitherto made their use for intravenous dosage forms extremely difficult.

Although peroral dosage forms, such as tablets or capsules, are becoming increasingly important, intravenous dosage forms still continue to be relevant in spite of certain disadvantages. The disadvantages which include administration only by a physician or specially authorized paramedical personnel and the special skills required of the person administering the drug, the "psychological" problems of the patient and his sensitivity to pain, and the complicated and expensive manufacture of those dosage forms, are offset by clear advantages in case of direct intravenous administration of a therapeutic agent, the metabolism in the gastrointestinal tract to which orally administered therapeutic agents are always subjected, can be substantially avoided. In particular, the so-called "first-pass effect" as a result of passage through the liver is miniraised. Some therapeutic agents, which would be insufficiently capable of oral absorption, can only be administered by the intravenous route. Other therapeutic agents can be administered intravenously in a less efficacious dose than is required for oral administration. Generally, in the case of life-threatening diseases, such as tumour diseases, intravenous administration is preferred, as the problem of absorption through the gastrointestinal tract in conjunction with undesired metabolism cannot be tolerated.

A suitable intravenous dosage form has not yet been available for the important group of therapeutic agents consisting of staurosporins and staurosporin derivatives. The object of the present invention, therefore, is to make available a suitable intravenous dosage form for staurosporin derivatives, especially N-benzoyl-staurosporin.

Numerous publications propose various means of converting a sparingly soluble therapeutic agent into a more soluble form that is suitable for intravenous formulations. Such a conversion can be carded out, for example, with the aid of so-called solubilisers, such as 1,2-propylene glycol or polyethylene glycol 300–400. Where lack of solubility is still a problem not overcome in spite of the use of the few solubilisers permitted in national pharmacopoeias, finely dispersed systems based on lipid mixtures are proposed in the prior art. In such systems, the sparingly soluble therapeutic agent is encapsulated in lipid particles of a particle size less than 1 µm and forms with the aqueous carder liquid a colloid-dispersed or preferably finely dispersed system which, although it is not a true molecularly dispersed solution, is nevertheless sufficiently homogeneous for an intravenous dosage form. Numerous publications propose the encapsulation of sparingly therapeutic agents in micelles, mixed micelles, inverse micelles or unilamellar or multilamellar liposomes. European Patent No. 406 162 (Weder et al.) describes a process for the preparation, in a high-pressure homogeniser, of nanoemulsions in which the average particle size of the dispersed lipids is less than 200 nm, and the use of these nanoemulsions for the preparation of intravenous dosage forms.

Surprisingly, it has been found that extremely sparingly soluble staurosporin derivatives can sufficiently be solubilised in nanoemulsions in the degree of homogeneity necessary for intravenous dosage forms.

The present invention relates to a pharmaceutical composition for the intravenous administration of staurosporin derivatives, comprising:

a) a staurosporin derivative which is sparingly soluble in water;

b) at least one substantially pure phospholipid of formula:

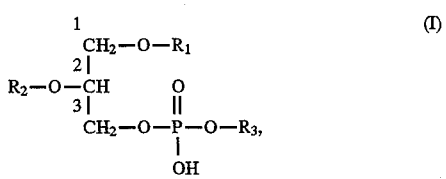

wherein $R_1$ is $C_{10-20}$acyl, $R_2$ is hydrogen or $C_{10-20}$acyl, $R_3$ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and hydroxy or $C_{2-5}$alkyl substituted by carboxy and amino, an inositol group or a glyceryl group, or a salt of such a compound;

c) a triglyceride of formula:

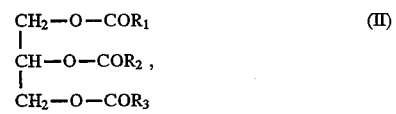

wherein $R_1$, $R_2$ and $R_3$ are $C_{8-24}$acyl;

d) a partial fatty acid ester of polyoxyethylene sorbitan;

e) the carrier liquid water, in the degree of purity necessary for intravenous administration; and, optionally, f) water-soluble excipients suitable for injection purposes, The pharmaceutical composition defined above is distinguished by useful phase properties of the solubilised therapeutic agent. For example, where opalescence and transparency occur in incident light, only an extremely slight milky turbidity enables it to be perceived that the nanoemulsion still has physical differences vis-a-vis the ideal state of a true molecular solution. These differences are acceptable, however, on account of the good homogeneity properties of the nanoemulsion. These properties can be detected, for example, in a surprisingly high storage stability, for example no phase separation after six months' storage at 2°–8° C. (by extrapolation, expected stability longer than two years), and surprisingly favourable toxicological properties. For example, 14-day toxicological experiments carried out on rats did not produce any negative results.

An especially preferred embodiment of the invention relates to a pharmaceutical composition comprising:

a) the therapeutic agent N-benzoyl-staurosporin;
b) purified lecithin from soybeans;
c) a triglyceride from the group of the neutral oils;
d) polyoxyethylene (20) sorbitan monooleate;
e) the carrier liquid water in the degree of purity necessary for intravenous administration; and, optionally,
f) water-soluble excipients suitable for injection purposes.

Within the scope of the description of the present invention, the terms used hereinbefore and hereinafter are defined as follows:

Component a): A staurosporin derivative sparingly soluble in water is described, for example, in U.S. Pat. No. 5 093 330 and is derived by additional substitution of the free hydrogen atom at the nitrogen of the N-methylamino substituent. Poor solubility in water is characteristic of staurosporin derivatives, thereby rendering them unsuitable for intravenous dosage forms. For example, the particularly effective N-benzoylstaurosporin has a water solubility of less than 0.1 mg/l at room temperature.

Suitable staurosporin derivatives are, for example, N-(3-nitrobenzoyl)-staurosporin, N-(3-fluorobenzoyl)-staurosporin, N-trifluoroacetylstaurosporin, N-phenylcarbamoylstaurosporin, N-(3-carboxypropionyl)-staurosporin, N-methylaminothiocarbonylstaurosporin, N-tert-butoxycarbonylstaurosporin, N-(4-carboxybenzoyl)-staurosporin, N-(3,5-dinitrobenzoyl)-staurosporin, N-(2-aminoacetyl)-staurosporin, N-alanylstaurosporin and also pharmaceutically acceptable salts of those derivatives. The N-benzoyl-staurosporin derivative is especially preferred.

Component b): The nomenclature of the phospholipids (I) and the numbering of the carbon atoms is in accordance with the recommendations given in Eur. J. of Biochem. 79, 11–21 (1977) "Nomenclature of Lipids" by the IUPAC-IUB Commission on Biochemical Nomenclature (CBN) (sn-nomenclature, stereospecific numbering).

$R_1$ and $R_2$ representing $C_{10-20}$acyl are preferably straight-chain $C_{10-20}$alkanoyl having an even number of carbon atoms and straight-chain $C_{10-20}$alkenoyl having a double bond and an even number of carbon atoms.

Straight-chain $C_{10-20}$alkanoyl $R_1$ and $R_2$ having an even number of carbon atoms are, for example, n-dodecanoyl, n-tetradecanoyl, n-hexadecanoyl or n-octadecanoyl.

Straight-chain $C_{10-20}$alkenoyl $R_1$ and $R_2$ having a double bond and an even number of carbon atoms are, for example, 6-cis- or 6-trans-, 9-cis- or 9-trans-dodecenoyl, -tetradecenoyl, -hexadecenoyl, -octadecenoyl or -icosenoyl, especially 9-cis-octadecenoyl (oleoyl), and also 9,12-cis-octadecadienoyl or 9,12,15-cis-octadecatdenoyl.

A phospholipid (I) wherein $R_3$ is 2-trimethylamino-1-ethyl is referred to by the trivial name lecithin and a phospholipid (I) wherein $R_3$ is 2-amino-1-ethyl is referred to by the trivial name cephalin. Especially useful are, for example, naturally occurring cephalin or lecithin, for example cephalin or lecithin from soybeans or chicken eggs having different or identical acyl groups $R_1$ and $R_2$, or mixtures thereof.

The phospholipid (I) may, however, alternatively be of synthetic origin. The term "synthetic phospholipid" is used to define phospholipids that have a uniform structure in respect of $R_1$ and $R_2$. Synthetic phospholipids of this type are preferably the above-mentioned lecithins and cephalins, wherein the acyl groups $R_1$ and $R_2$ have a defined structure and are derived from a fatty acid of defined structure having a degree of purity greater than approximately 95%. $R_1$ and $R_2$ may be identical or different and unsaturated or saturated groups. Preferably, $R_1$ is saturated, for example n-hexadecanoyl, and $R_2$ is unsaturated, for example, 9-cis-octadecenoyl (oleoyl).

The term "naturally occurring" phospholipid (I) defines phospholipids that do not have a uniform composition in respect of $R_1$ and $R_2$. Such natural phospholipids are likewise lecithins and cephalins of which the acyl groups $R_1$ and $R_2$ are structurally undefined and are derived from naturally occurring fatty acid mixtures.

The definition "substantially pure" phospholipid (I) defines a degree of purity of more than 90 % (by weight), preferably more than 95 %, of the phospholipid (I), which can be established by suitable methods of analysis, for example paper chromatography, thin-layer chromatography, HPLC or enzymatic colour testing.

In a phospholipid (I), $R_3$ representing $C_{1-4}$alkyl is, for example, methyl or ethyl. The definition methyl is preferred.

$R_3$ groups representing $C_{1-5}$alkyl substituted by carboxy, $C_{2-5}$alkyl substituted by hydroxy, or $C_{2-5}$alkyl substituted by carboxy and hydroxy are, for example, 2-hydroxyethyl, 2,3-dihydroxy-n-propyl, carboxymethyl, 1- or 2-carboxyethyl, dicarboxymethyl, 2-carboxy-2-hydroxyethyl or 3-carboxy-2,3-dihydroxy-n-propyl.

$R_3$ representing $C_{2-5}$alkyl substituted by carboxy and amino is, for example, 3-amino-3-carboxy-n-propyl or 2-amino-2-carboxy-n-propyl, preferably 2-amino-2-carboxyethyl. Phospholipids (I) having those groups may be in salt form, for example in the form of the sodium or potassium salt.

Phospholipids (I) wherein $R_3$ is an inositol or glyceryl group are known by the names phosphatidylinositol and phosphatidylglycerol.

The following names given in brackets are also customary for the acyl groups present in the phospholipids (I) and in the triglycerides (II):

9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis-octadecenoyl (oleoyl), 9-trans-octadecenoyl (elaidoyl), 9,12-cis-octadecadienoyl (linoleoyl), 9,12,15-cis-octadecatrienoyl (linolenoyl),11-cis-octadecenoyl (vaccenoyl), 9-cis-icosenoyl (gadoleoyl), 5,8,11,14-Sis-eicosatetraenoyl (arachidonoyl), n-dodecanoyl (lauroyl), n-tetra-decanoyl (myristoyl), n-hexadecanoyl (palmitoyl), n-octadecanoyl (stearoyl), n-icosanoyl (arachidoyl), n-docosanoyl (behenoyl), n-tetracosanoyl (lignoceroyl).

A salt of the phospholipid (I) is preferably pharmaceutically acceptable. Salts are defined by the presence of salt-forming groups in the substituent $R_3$ and also by the free hydroxy group on the phosphorus atom. The formation of inner salts is also possible. Alkali metal salts, especially sodium salts, are preferred.

In an especially preferred embodiment, purified lecithin from soybeans is used.

Component c): In a triglyceride of formula II used as component c), $R_1$, $R_2$ and $R_3$ are straight-chain $C_{8-24}$acyl having an even number of carbon atoms, especially n-octanoyl, n-dodecanoyl, n-tetradecanoyl, n-hexadecanoyl, n-octadecanoyl, 9-cis-dodecenoyl, 9-cis-tetradecenoyl, 9-cis-hexadecenoyl, 9-cis-octadecenoyl or 9-cis-icosenoyl. The definitions of $R_1$, $R_2$ and $R_3$ may be identical or different, whereas the individual groups $R_1$, $R_2$ and $R_3$ themselves are being defined by their uniform structure, which is characteristic of synthetic or semi-synthetic trilycerides. $R_1$, $R_2$ and $R_3$ may, however, alternatively consist of various acyl groups of different structures, which is characteristic of triglycerides of natural origin.

A triglyceride of formula II is a semi-synthetic or synthetic, substantially pure triglyceride or a pharmaceutically acceptable triglyceride of natural origin. A trilyciride of natural origin is preferred, for example groundnut, sesame, sunflower, olive, maize kernel, soybean, castor, cottonseed, rape, thistle, grapeseed, fish or coconut oil. In an especially preferred embodiment of the invention, a triglyceride having different acyl groups of different structure defined by the term "neutral oil" is used, for example a trilyciride of fractionated coconut $C_8$-$C_{10}$ fatty acids of the Miglyol®type, e.g. MIGLYOL 812.

Component d): The mentioned partial fatty acid ester of polyoxyethylene sorbitan consists preferably of a substantially pure ester of sorbitan or a mixture of different esters of sorbitan in which the structure of the fatty acid groups and the length of the polyoxyethylene chains may vary. The hydrophilic sorbitan is preferably etherified by three hydrophilic polyoxyethylene chains and esterified by a hydrophobic fatty acid group. The sorbitan may, however, alternatively be etherified by only one or two polyoxyethylene chains and correspondingly esterified by two or three fatty acid groups. The basic sorbitan structure is altogether substituted by a minimum of two and a maximum of three hydrophilic groups, the term "hydrophilic group" embracing the polyoxyethylene chains, whereas the fatty acid groups are hydrophobic.

The polyoxyethylene chain is linear and has preferably from 4 to 10, especially from 4 to 8, ethylene oxide units. The ester groups on the basic sorbitan structure are derived from a saturated or unsaturated, straight-chain carboxylic acid having an even number of from 8 to 20 carbon atoms. The ester group derived from that carboxylic acid is preferably straight-chained having 12, 14, 16 or 18 carbon atoms, for example n-dodecanoyl, n-tetradecanoyl, n-hexadecanoyl or n-octadecanoyl. The ester group derived from an unsaturated carboxylic acid having an even number of from 8 to 20 carbon atoms is preferably straight-chained having 12, 14, 16 or 18 carbon atoms, for example oleoyl. The mentioned esters of sorbitan are inconformity with the data given in the British Pharmacopoeia (specialised monograph) or Ph. Helv. VI. In particular the product specifications published by the mentioned manufacturers with the information on data sheets for the relevant product, especially specifications such as shape, colour, HLB value, viscosity, ascending melting point and solubility, apply.

Suitable partial fatty acid esters of polyoxyethylene sorbitan are commercially obtainable under the trademark Tween® of ICI Corp. and known by the chemical names polyoxyethylene (20 or 4) sorbitan monolaurate (TWEEN 20 and 21 ), polyoxyethylene (20) sorbitan monopalmitate or monostearate (TWEEN 40 and 60), polyoxyethylene (4 or 20) sorbitan monostearate or tristearate (TWEEN 61 and 65), polyoxyethylene (20 or 5) sorbitan monocleate (TWEEN 80 or 81 ) and polyoxyethylene (20) sorbitan trioleate (TWEEN 85).

In an especially preferred embodiment of the invention, polyoxyethylene (20) sorbitan monocleate (TWEEN 80) is used as component d).

Component e), the carrier liquid water having the degree of purity necessary for intravenous administration is, in accordance with the regulations of national pharmacopoeias, germ- and pyrogen-free.

Component f), water-soluble excipients suitable for injection purposes, is present in the pharmaceutical composition if desired. Suitable excipients are those for the production of isotonic conditions, for example ionic excipients, e.g. sodium chloride, or other water-soluble excipients, e.g. sorbitan, mannitol, glucose, lactose or fructose.

The present invention also relates to the process for the preparation process for the pharmaceutical composition, which is know per se and comprises preparing a liposome dispersion containing the phospholipid of formula I and, optionally, water-soluble excipients, preparing an oily homogeneous mixture consisting of the sparingly soluble staurosporin derivative, the triglyceride of formula II and the partial fatty acid ester of polyoxyethylene sorbitan, mixing together the aqueous liposome dispersion and the oily homogeneous mixture, subjecting the obtainable mixture to the conditions of high-pressure homogenisation, and subjecting the obtainable clear dispersion to the following subsequent operations:

α) addition of an additional amount of water as carrier liquid and also, optionally, of further water-soluble excipients suitable for injection purposes, filtration and, where appropriate, dialysis of the clear dispersion; or β) filtration and, where appropriate, dialysis, and subsequent conversion of the obtainable clear dispersion into a dry preparation, optionally with the addition of water-soluble excipients, and reconstitution of the dry preparation to form an injectable dispersion.

In an especially preferred process variant, an intravenously administrable nanoemulsion is prepared using the sparingly water-soluble staurosporin derivative N-benzoyl-staurosporin.

The formulation base that can be used for that process, consists of the following components:

b) at least one substantially pure phospholipid of formula:

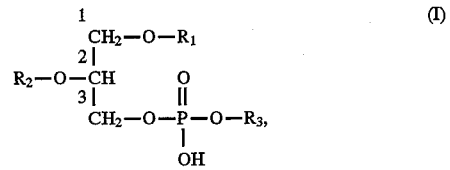

wherein $R_1$, $R_2$ and $R_3$ are as defined, or a salt of such a compound;

c) a triglyceride of formula:

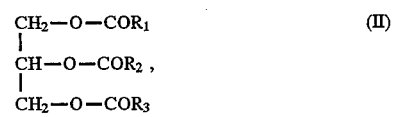

wherein $R_1$, $R_2$ and $R_3$ are as defined;

d) a partial fatty acid ester of polyoxyethylene sorbitan;

e) the carrier liquid water in the degree of purity necessary for intravenous administration; and, where appropriate, f) water-soluble excipients suitable for injection purposes;

That formulation base is useful for intravenous dosage forms and other dosage forms in which the solubilisation of a sparingly soluble active ingredient is necessary, for example for capsule fillings, drops, lotions or emulsions for ointments, creams etc.

It is also possible to add to the formulation base additional excipients characteristic of those dosage forms. The formulation base is useful for the solubilisation of sparingly soluble staurosporin derivatives in accordance with the above-mentioned object of the invention and also for the solubilisation of other sparingly soluble therapeutic agents.

Especially preferred is the formulation base comprising:

b) purified lecithin from soybeans;

c) a triglyceride from the group of the neutral oils;

d) polyoxyethylene (20) sorbitan monooleate;

e) the carrier liquid water having the degree of purity necessary for intravenous administration; and, optionally, f) water-soluble excipients suitable for injection purposes.

The aqueous liposome dispersion comprising the phospholipid component b) of formula I is prepared by using a process for the preparation of liposomes which is known per se, for example by homogenising a coarse aqueous dispersion comprising the phospholipid component b) by intensive shaking using a dispersing apparatus, for example a Vortex mixer, static mixers or dispersing apparatus of the POLY-TRON type (Kinematica AG, Littau CH) or dispersing apparatus from EKA (DE-Staufen). By such means liposomes are formed that may be large, small, unilamellar or multilamellar. Approximately from 0.1 to 50.0% by weight, based on the total weight of the aqueous dispersion in that preliminary stage of the process, preferably approximately from 2.0 to 20.0 % by weight, are dispersed in the aqueous phase. During the preparation of the liposome dispersion, the so-called phase-transition temperature (gel-like/liquid crystalline) of the phospholipids used is critical. The dispersion is carded out preferably at temperatures at which the phospholipids are in the liquid crystalline state, (hat is to say above the so-called phase-transition temperature. Phospholipids that are in the liquid crystalline state at room temperature or lower temperatures are especially suitable. The liposomes are, where appropriate, prepared at temperatures below room temperature and/or under an inert gas atmosphere.

The size and structure (multilamellar-unilamellar) of the liposomes formed in that preliminary stage depend, inter alia, on the amount of phospholipid component used and on the choice of process. In the case of shaking or stirring, for example using conventional stirrers having a propeller or wing blade, or using a magnetic stirrer, dispersions containing a high proportion of large multilamellar liposomes are obtained. Increasing the stirring frequency or transferring to phase mixers with high shearing forces causes an increase in the proportion of small multilamellar liposomes. Treatment with supersonic waves results in a high proportion of unilamellar liposomes in the dispersion.

The oily homogeneous mixture consisting of the therapeutic agent being the staurosporin derivative, especially N-benzoyl-staurosporin, the triglyceride of formula II and the partial fatty acid ester of polyoxyethylene sorbitan is prepared by mixing the components and shaking or stirring, for example using conventional stirrers with a propeller or wing blade or using a magnetic stirrer or phase mixers, which are commercially obtainable, for example, from Vortex. In order to obtain an especially homogeneous mixture, stirring is carded out at high speed, for example using stirrers from Polytron, e.g. POLYTRON PT 3000 or DH 30/30.

The subsequent preparation of the pharmaceutical composition is effected by mixing the aqueous liposome dispersion with the oily homogeneous mixture (oil phase). Preferably, from 0.05 to 0.4 parts by weight of phospholipid (I) is mixed with each part by weight of the oily phase. During mixing, first of all an emulsion is formed, which is processed further in a high-pressure homogeniser. Under the conditions of high-pressure homogenisation, a dispersion characterized by physicochemical properties that are definable by the term "nanoemulsion" is formed. A nanoemulsion may be defined as a highly disperse two-phase colloid system. The amphiphilic particles present in the dispersion can be differentiated from other structures, such as liquid crystals, micelles, inverse micelles or liposomes, by means of laser light-scattering measurements and examination using an electron microscope. For the statistical majority of more than 90 %, preferably more than 95 % of particles, a mean particle size smaller than 20 nm is characteristic. The therapeutic agent, in this case the sparingly water-soluble staurosporin derivative, is encapsulated in the amphiphilic particles of the nanoemulsion.

Suitable high-pressure homogenisers are the commercially available products, for example, from Rannie (APV Rannie AS, Albertslund DK) or Gaulin (APV Gaulin Intern. BV, Hilversum NL), especially the Rannie High Pressure Laboratory Homogeniser Mini-Lab model, type 8.30H. The pressure applied is in the range of approximately from 500–1000 bar, preferably approximately from 600–800 bar. Similarly, the preferred process temperature is the range in which the phospholipids present in the nanoemulsion are in the liquid crystalline state, which is approximately from 0° to 40° C., especially from 20° to 30° C.

Methods known per se, for example optical analysis, are suitable for the characterisation of the nanoemulsions obtained: weak to strong opalescence of the preparation is readily recognisable (indication of average particle size smaller than 50 nm); laser light-scattering (determination of the particle size and homogeneity); electron microscopy (freeze fracture and negative contrast technique).

Subsequent operations:

The necessary amount of water, which must have the prescribed degree of purity for injections, may be added to the nanoemulsion. After selection of a filtration method suitable for such dispersions, for example sterile gel filtration, e.g. with Sepharose® or Sephacryl® (Pharmacia) as carrier, or preferably sterile filtration (0.2 µm), e.g. with PAL filter (Gelman), and, optionally, after addition of further water-soluble excipients suitable for intravenous dosage forms, the nanoemulsion is administrable directly. Especially by means of sterile filtration, it is possible to separate off all relatively large particles of a diameter greater than approximately 200 nm contained in the dispersion, as well as suspended substances and solids and excess dispersed lipids that may be present in high-molecular-weight aggregate. This produces a nanoemulsion with a proportion of hydrophilic particles having a relatively uniform size. Alternatively or in addition to sterile filtration, the nanoemulsion can be dialysed and/or subjected to ultrafiltration for the purpose of purification.

As an alternative to the preparation of a directly administrable nanoemulsion, the subsequent purification steps described above may be carried out and the purified nanoemulsion may be converted into a dry preparation, especially a lyophilisate, which is reconstituted before administration by the addition of water. After reconstitution of the lyophilisate an administrable nanoemulsion is again obtained. For the preparation of lyophilisates, the addition of so-called builders, such as lactose of mannitol, is customary. That excipient is added in such an amount that after reconstitution of the lyophilisate the nanoemulsion to be administered has isotonic properties.

Measured amounts of nanoemulsion are filled, optionally in the form of a concentrate, into containers suitable for a unit dose, e.g. glass ampoules (vials). The filled containers may, if desired, be cooled to approximately from −40° to −50° C., especially to approximately −45° C., and then lyophilised at a pressure of approximately from 0.2 to 0.6 mbar by slowly heating to a final temperature of approximately from 25° to 35° C.

The pharmaceutical compositions described hereinbefore may be used as intravenously administrable therapeutic agents in the treatment of disorders that are caused by malignant cell growth. They are suitable especially as tumour inhibitors, as anti-inflammatory agents, as antibiotics, and in the treatment of arteriosclerosis, or can be used therapeutically in various disorders of the cardiovascular system and central nervous system.

The following Example illustrates the invention:

EXAMPLE a) Formulation for one unit dose:

| | |
|---|---|
| 1.0 mg | N-benzoyl-staurosporin |
| 5.5 mg | lecithin from soybean oil (LIPOID S 100) |
| 11.1 mg | neutral oil MIGLYOL 812 |
| 16.6 mg | PS 80: TWEEN 80. | b) Quantities for a 5 kg batch:

| | |
|---|---|
| 9.0 g | N-benzoyl-staurosporin |
| 50.0 g | lecithin from soybean oil (Lipold S 100) |
| 100.0 g | neutral oil MIGLYOL 812 |
| 150.0 g | PS 80: TWEEN 80. |

Using a stirrer supplied by Polytron, e.g. POLYTRON PT 3000 or DH 30/30, an oily homogeneous mixture consisting of N-benzoyl-staurosporin, the neutral oil and TWEEN 80 is prepared. The lecithin from soybean oil (Lipold S 100) is placed in a round-bottomed flask and mixed with water for injection. Dispersion is carded out using a dispersing apparatus of the POLYTRON type (pH 6–8, room temperature, 10 000 revs/min, final temperature 25°–27° C., 7 min.). After mixing the oily suspension with the aqueous liposome dispersion, the mixture is subjected to high-pressure homogenisation in a Ronnie High Pressure Laboratory Homogeniser Mini-Lab, type 8.30H in three cycles each lasting 25 minutes long. Pressure conditions of approximately 600 bar are established. The selected process temperature is in the range of from 30° to 33° C. The resulting nanoemulsion is then sterile-filtered over a 0.2 μm PAL filter.

What is claimed is:

1. A pharmaceutical composition for the intravenous administration of a staurosporin derivative, comprising:
   a) a staurosporin derivative which is sparingly soluble in water;
   b) at least one substantially pure phospholipid of formula:

$$\begin{array}{c} \overset{1}{C}H_2-O-R_1 \\ \overset{2}{|} \\ R_2-O-\overset{3}{C}H \quad\quad O \\ \overset{}{|} \quad\quad\quad\quad \| \\ CH_2-O-P-O-R_3, \\ | \\ OH \end{array} \quad (I)$$

wherein $R_1$ is $C_{10-20}$acyl, $R_2$ is hydrogen or $C_{10-20}$acyl, $R_3$ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and hydroxy or $C_{2-5}$alkyl substituted by carboxy and amino, an inositol group or a glyceryl group, or a salt of such a compound;

c) a triglyceride of formula:

$$\begin{array}{c} CH_2-O-COR_1 \\ | \\ CH-O-COR_2, \\ | \\ CH_2-O-COR_3 \end{array} \quad (II)$$

wherein $R_1$, $R_2$ and $R_3$ are $C_{8-24}$acyl;

d) a partial fatty acid ester of polyoxyethylene sorbitan;

e) the carrier liquid water, in the degree of purity necessary for intravenous administration; and, optionally, f) water-soluble excipients suitable for injection purposes.

2. A pharmaceutical composition according to claim 1, comprising:
   a) the therapeutic agent N-benzoyl-staurosporin;
   b) purified lecithin from soybeans;
   c) a triglyciride from the group of the neutral oils;
   d) polyoxyethylene (20) sorbitan monooleate;
   e) the carrier liquid water in the degree of purity necessary for intravenous administration; and, optionally,
   f) water-soluble excipients suitable for injection purposes.

3. A process for the preparation of a pharmaceutical composition according to claim 1, for the intravenous administration of a sparingly soluble staurosporin derivative, which comprises preparing a liposome dispersion containing the phospholipid of formula I and, optionally, water-soluble excipients, preparing an oily homogeneous mixture consisting of the sparingly soluble staurosporin derivative, the triglyceride of formula II and the partial fatty acid ester of polyoxyethylene sorbitan, mixing together the aqueous liposome dispersion and the oily homogeneous mixture, subjecting the obtainable mixture to the conditions of high-pressure homogenisation, and subjecting the obtainable clear dispersion to the following subsequent operations:

α) addition of an additional amount of water as carrier liquid and also, optionally, of further water-soluble excipients suitable for injection purposes, filtration and, where appropriate, dialysis of the clear dispersion; or β) filtration and, where appropriate, dialysis, and subsequent conversion of the obtainable clear dispersion into a dry preparation, optionally with the addition of water-soluble excipients, and reconstitution of the dry preparation to form an injectable dispersion.

4. A process according to claim 3, which comprises preparing an intravenously administrable nanoemulsion using the sparingly water-soluble staurosporin derivative N-benzoyl-staurosporin.

5. A nanoemulsion obtainable in accordance with the process according to claim 3 comprising a staurosporin derivative sparingly soluble in water.

6. A nanoemulsion obtainable in accordance with the process according to claim 3 comprising N-benzoyl-staurosporin.

7. A concentrate or dry preparation obtainable in accordance with the process according to claim 3.

* * * * *